United States Patent
Onochi et al.

(10) Patent No.: US 11,964,265 B2
(45) Date of Patent: Apr. 23, 2024

(54) METHANATION CATALYST PROCESSING METHOD, METHANE PRODUCING METHOD, AND METHANATION CATALYST

(71) Applicant: TOYOTA JIDOSHA KABUSHIKI KAISHA, Toyota (JP)

(72) Inventors: Yusaku Onochi, Toyota (JP);
Masakazu Aoki, Nagakute (JP);
Mitsuru Matsumoto, Nagakute (JP);
Takuto Hirose, Nagakute (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 18/307,060

(22) Filed: Apr. 26, 2023

(65) Prior Publication Data
US 2023/0381768 A1 Nov. 30, 2023

(30) Foreign Application Priority Data
May 24, 2022 (JP) .................. 2022-084810

(51) Int. Cl.
*B01J 37/14* (2006.01)
*B01J 23/755* (2006.01)
*C07C 1/12* (2006.01)

(52) U.S. Cl.
CPC ............. *B01J 37/14* (2013.01); *B01J 23/755* (2013.01); *C07C 1/12* (2013.01); *C07C 2523/755* (2013.01)

(58) Field of Classification Search
CPC ..... C07C 1/12; C07C 2523/755; B01J 23/755
See application file for complete search history.

(56) References Cited

U.S. PATENT DOCUMENTS

2012/0046512 A1* 2/2012 Gauthier ................. C07C 7/167
585/841
2019/0344246 A1 11/2019 Mori et al.

FOREIGN PATENT DOCUMENTS

JP 2018122247 A 8/2018
JP 2019155227 A 9/2019

OTHER PUBLICATIONS

Mutz et al., surface modification of supported Ni particles and its impact on the catalytic performance during dynamically operated methanation of carbon dioxide (Catalysis 2017,7, 279 pp. 1-18).*

* cited by examiner

*Primary Examiner* — Jafar F Parsa
(74) *Attorney, Agent, or Firm* — Dickinson Wright, PLLC

(57) ABSTRACT

Provided is a methanation catalyst processing method capable of suppressing degradation of a catalyst performance. A methanation catalyst processing method of the present disclosure includes oxidizing nickel through a heat treatment of a methanation catalyst by supplying an oxygen gas containing oxygen to a reactor, the reactor housing the methanation catalyst containing the nickel as a catalyst component. In the oxidizing, the oxygen gas is supplied to the reactor such that the oxygen is supplied to 1 g of the methanation catalyst at a supply rate in a range of from 0.0213 mmol-$O_2$/sec·g-cat. to 0.0638 mmol-$O_2$/sec·g-cat., and a time period of the heat treatment of the methanation catalyst by supplying the oxygen gas to the reactor is set to 30 minutes or more.

1 Claim, 17 Drawing Sheets

Operation Stop

METHANATION CATALYST PROCESSING METHOD, METHANE PRODUCING METHOD, AND METHANATION CATALYST

CROSS REFERENCE TO RELATED APPLICATIONS

The present application claims priority from Japanese patent application JP 2022-084810 filed on May 24, 2022, the entire content of which is hereby incorporated by reference into this application.

BACKGROUND

Description of Related Art

The present disclosure relates to a methanation catalyst processing method used in generating methane ($CH_4$) from carbon dioxide ($CO_2$) and hydrogen ($H_2$) through a methanation reaction, a methane producing method using the processing method, and a methanation catalyst.

Background Art

To suppress global warming, the efforts to reduce carbon dioxide as a greenhouse gas have been performed. As one of the efforts, there has been known an effort that utilizes carbon dioxide by a methanation reaction generating methane through a thermochemical reaction of carbon dioxide with hydrogen.

In the methanation reaction, a methane producing method using a methanation catalyst that accelerates the reaction of carbon dioxide with hydrogen is used. As the methane producing method using a methanation catalyst, for example, as disclosed in JP 2018-122247 A and JP 2019-155227 A, producing methods using a methanation catalyst containing nickel (Ni) as a catalyst component have been known.

In the methane producing method using a methanation catalyst disclosed in JP 2018-122247 A, a stabilized zirconia carrier in which a stabilizing element is solid-solved in zirconia is applied as a carrier on which nickel as a catalyst component is supported in the methanation catalyst, and an inorganic oxide is added for the purpose of suppressing aggregation of the nickel supported by the carrier, thereby intending to improve the methane producing speed.

On the other hand, in the methane producing method using a methanation catalyst disclosed in JP 2019-155227 A, in the methanation catalyst, a carrier on which nickel as a catalyst component is supported contains one or more selected from the group consisting of Ce, La, Pr, Nd, Pm, Sm, Eu, Gd, Tb, Dy, Ho, Er, Tm, Yb, and Lu, thereby enabling conversion of carbon dioxide to methane at less than 300° C. with high efficiency.

SUMMARY

On the other hand, for example, when methane is produced through the methanation reaction with the conventional methane producing method using a methanation catalyst containing nickel as a catalyst component, as disclosed in JP 2018-122247 A, JP 2019-155227 A, and the like, there is a period in which the operation of the production facility is stopped for the maintenance of the production facility, a non-working day, or the like. During the facility operation stop period, the atmosphere enters a reaction system inside a reactor in which the methanation catalyst is placed from the outside of the reactor in some cases. In this situation, since a large part of nickel contained in the methanation catalyst is reduced and present as metallic nickel (metallic Ni) after the methanation reaction in the reactor, the nickel is easily oxidized. Consequently, during the facility operation stop period, the metallic nickel in the methanation catalyst is rapidly oxidized by oxygen in the atmosphere entering the reaction system inside the reactor from the outside of the reactor, and becomes nickel oxide (NiO), thereby reducing the activity of the catalyst. Further, the aggregation of the carrier or nickel or the like caused by the heat generation due to the rapid oxidation reaction of metallic nickel deteriorates the catalyst, thus possibly decreasing the catalyst performance. Especially, for example, when the methanation catalyst contacts the atmosphere in a high temperature state exceeding about 50° C., the possibility is high. When the methanation catalyst is, for example, at a low temperature of about 50° C. or less, the oxidation reaction of nickel is less likely to progress even when the methanation catalyst contacts the atmosphere. However, for example, in warm-temperate regions including Japan and the like, since the reaction system in the reactor easily becomes a high temperature state especially in a high temperature season such as summer, such a problem is likely to occur.

As a countermeasure against the problem, the following method is considered. During the facility operation stop period, for example, an inert gas such as nitrogen ($N_2$) is flown to the reaction system in the reactor in which the methanation catalyst containing nickel is placed, thereby removing the atmosphere entering the reaction system. However, such a countermeasure arises an additional problem that the running cost necessary for flowing the inert gas to the reaction system in the reactor increases.

The present disclosure has been made in consideration of the above-described problems, and provides a methanation catalyst processing method, a methane producing method, and a methanation catalyst capable of suppressing degradation of catalyst performance.

To solve the above-described problems, a methanation catalyst processing method of the present disclosure comprises oxidizing nickel through a heat treatment of a methanation catalyst by supplying an oxygen gas containing oxygen to a reactor, the reactor housing the methanation catalyst containing the nickel as a catalyst component. In the oxidizing, the oxygen gas is supplied to the reactor such that the oxygen is supplied to 1 g of the methanation catalyst at a supply rate in a range of from 0.0213 mmol-$O_2$/sec·g-cat. to 0.0638 mmol-$O_2$/sec·g-cat., and a time period of the heat treatment of the methanation catalyst by supplying the oxygen gas to the reactor is set to 30 minutes or more.

A methane producing method of the present disclosure comprises: processing of oxidizing the nickel through the heat treatment of the methanation catalyst housed in the reactor in the oxidizing using the above-described methanation catalyst processing method; and generating methane by supplying a raw material gas containing carbon dioxide and hydrogen to the reactor housing the methanation catalyst in which the nickel has been oxidized in the processing.

Furthermore, a methanation catalyst of the present disclosure comprises nickel as a catalyst component. The nickel is present as a metallic nickel and a nickel oxide, and a weight ratio of a content of the metallic nickel to a total content of the metallic nickel and the nickel oxide is in a range of from 58 weight % to 67 weight %.

Effect

The present disclosure can suppress the degradation of the catalyst performance.

Problems, configurations, and effects of the present disclosure other than ones described above will be clarified in the following explanation of embodiments.

DETAILED DESCRIPTION OF THE EMBODIMENTS

Figure 1:
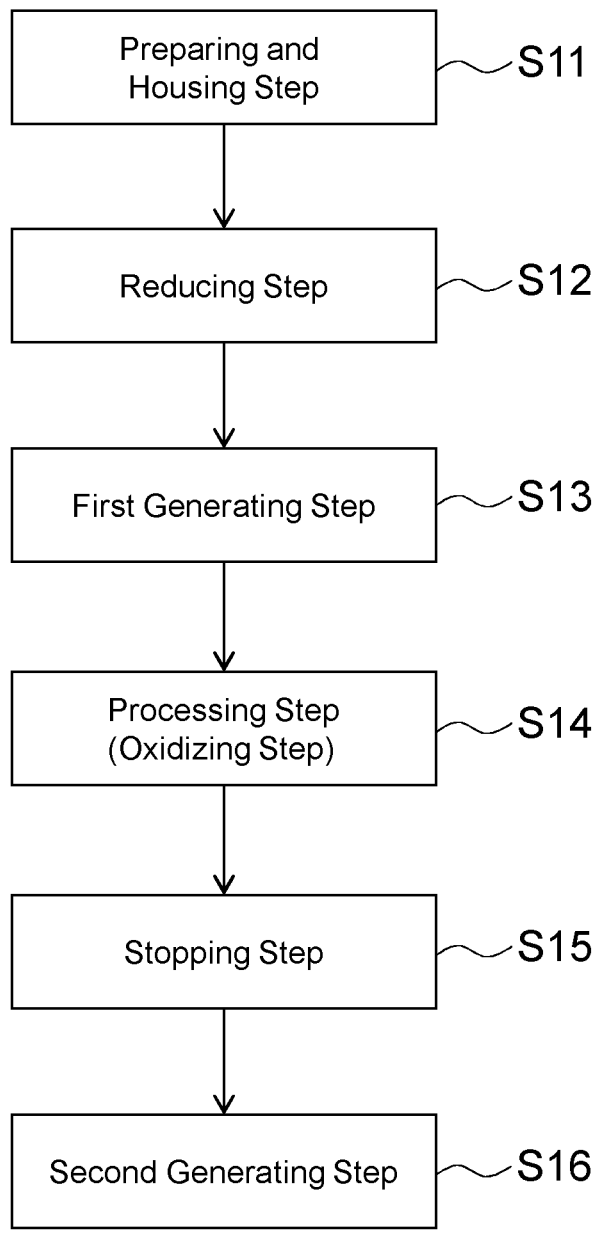
FIG. 1 is a flowchart illustrating an outline of the methane producing method according to the one embodiment.

The following describes embodiments according to a methanation catalyst processing method, a methane producing method, and a methanation catalyst of the present disclosure by referring to the drawings and the like. The following description indicates specific examples of the content of the present disclosure, the present disclosure is not limited thereto, and various changes and modifications by those skilled in the art can be made within the scope of the technical ideas disclosed in the Description. In all the drawings for describing the present disclosure, same reference numerals are attached to those having the same functions, and their repeated descriptions will be omitted in some cases.

In the Description, "to" is used in the meaning which is construed as including numerical values described before and after "to" as a lower-limit value and an upper-limit value. In a plurality of numerical ranges described in stages in the Description, an upper-limit value and a lower-limit value described in one numerical range may be replaced with an upper-limit value and a lower-limit value in another numerical range, respectively. The upper-limit values and the lower-limit values in the numerical ranges described in the Description may be replaced with upper-limit values and lower-limit values indicated in the examples, respectively.

First, the outline of a methanation catalyst processing method, a methane producing method, and a methanation catalyst according to the embodiments will be described with an example of a methanation catalyst processing method, a methane producing method, and a methanation catalyst according to one embodiment.

FIG. 1 is a flowchart illustrating an outline of the methane producing method according to the one embodiment. FIG. 2A to FIG. 2F are process cross-sectional views illustrating the outline of the methane producing method according to the one embodiment.

Figure 2A:
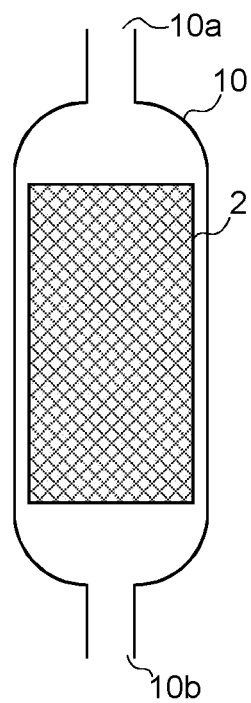
FIG. 2A is a process cross-sectional view illustrating the outline of the methane producing method according to the one embodiment.

In the methane producing method according to the one embodiment, first, as illustrated in FIG. 1 and FIG. 2A, a methanation catalyst 2 containing a carrier and nickel supported on carrier particles is prepared as a methanation catalyst 2 containing nickel (Ni) as a catalyst component, and the methanation catalyst 2 is housed in a reactor 10 of a methane production facility (not illustrated) (preparing and housing step S11). Since the prepared methanation catalyst 2 is sintered under an oxygen atmosphere in the synthesis, nickel is present as not only metallic nickel (metallic Ni) but also nickel oxide (NiO). Therefore, to cause nickel to sufficiently provide a catalytic action in a methanation reaction, it is necessary to reduce nickel oxide to make metallic nickel.

Figure 2B:
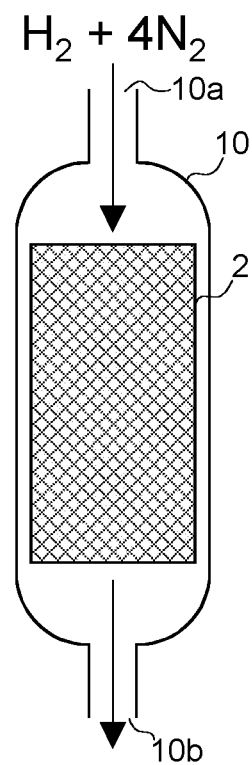
FIG. 2B is a process cross-sectional view illustrating the outline of the methane producing method according to the one embodiment.

Therefore, next, as illustrated in FIG. 1 and FIG. 2B, a reducing gas containing, for example, 20 volume % of hydrogen ($H_2$) and 80 volume % of nitrogen ($N_2$) at a high temperature of, for example, 400° C. is supplied to the reactor 10 via a gas inlet 10a, thereby flowing the reducing gas around the methanation catalyst 2. Accordingly, nickel oxide in the methanation catalyst 2 is reduced to metallic nickel (reducing step S12).

Figure 2C:
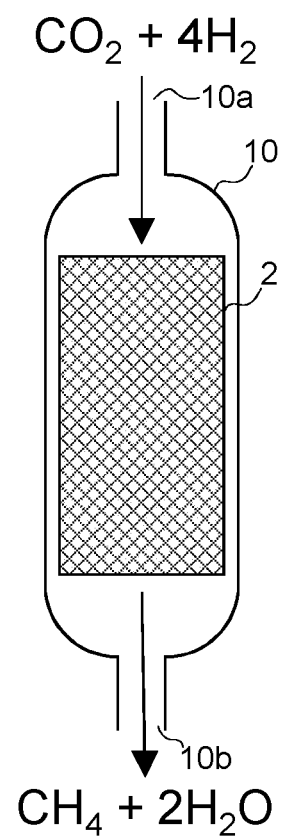
FIG. 2C is a process cross-sectional view illustrating the outline of the methane producing method according to the one embodiment.

Next, as illustrated in FIG. 1 and FIG. 2C, after ending the reducing step by stopping the supply of the reducing gas to the reactor, the temperature of the methanation catalyst is decreased to equal to or less than a temperature of a raw material gas at the gas inlet of the reactor in a later first generating step, and subsequently, the raw material gas containing 20 volume % of carbon dioxide ($CO_2$) and 80 volume % of hydrogen ($H_2$) is supplied to the reactor via the gas inlet 10a. At this time, by supplying the heated raw material gas to the reactor the heated raw material gas is flown around the methanation catalyst 2. This causes a methanation reaction to generate methane ($CH_4$) (first generating step S13). At this time, since the methanation reaction causes a reduction action to the methanation catalyst 2, an action that reduces nickel oxide remaining in the methanation catalyst 2 to metallic nickel occurs. Methane is flown out from a gas outlet 10b of the reactor 10 together with simultaneously generated water ($H_2O$).

Figure 2D:
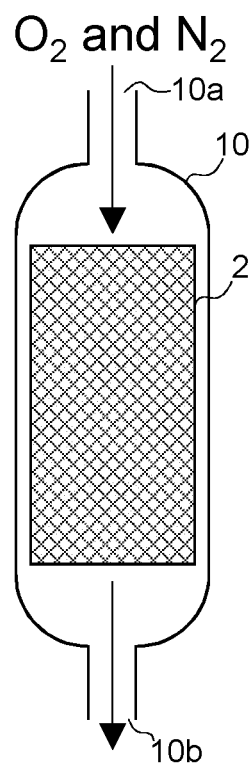
FIG. 2D is a process cross-sectional view illustrating the outline of the methane producing method according to the one embodiment.

Next, as illustrated in FIG. 1 and FIG. 2D, after stopping the methanation reaction by stopping the supply of the raw material gas to the reactor 10, the temperature of the methanation catalyst 2 is decreased to equal to or less than a temperature of an oxygen gas at the gas inlet 10a of the reactor 10 in a later oxidizing step, and subsequently, using a processing method for processing the methanation catalyst 2 according to the one embodiment, the oxygen gas containing oxygen and nitrogen is supplied to the reactor 10 via the gas inlet 10a to flow the oxygen gas around the methanation catalyst 2, thereby performing a heat treatment of the methanation catalyst 2. At this time, the oxygen gas is heated to make the oxygen gas temperature at the gas inlet 10a of the reactor 10 within a range of from 60° C. to 150° C. Additionally, the oxygen concentration of the oxygen gas is adjusted to a range of from 1 volume % to 3 volume %, and the oxygen gas is supplied to the reactor 10 such that oxygen is supplied to 1 g of the methanation catalyst 2 at a supply rate in a range of from 0.0213 mmol-$O_2$/sec·g-cat. to 0.0638 mmol-$O_2$/sec·g-cat. The pressure inside the reactor 10 is set to 1 atm (atmospheric pressure). Furthermore, a time period of the heat treatment of the methanation catalyst 2 by supplying the oxygen gas to the reactor 10 is set to 30 minutes or more. By thus performing the heat treatment of the methanation catalyst 2, a surface part of metallic nickel is oxidized, thereby forming a nickel oxide film containing nickel oxide (NiO) (processing step (oxidizing step) S14). The methanation catalyst 2 in which the nickel oxide film has been formed on the surface part of metallic nickel in the processing step contains nickel as a catalyst component. The nickel is present as metallic nickel and nickel oxide, and a weight ratio of a content of a metallic nickel to a total content of the metallic nickel and the nickel oxide is within a range of, for example, from 58 weight % to 67 weight %.

Figure 2E:
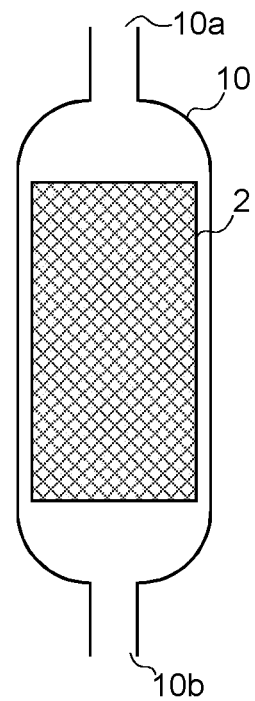
FIG. 2E is a process cross-sectional view illustrating the outline of the methane producing method according to the one embodiment.

Next, as illustrated in FIG. 1 and FIG. 2E, the processing step (oxidizing step) is ended by stopping the supply of the oxygen gas to the reactor 10, thereby stopping the operation of the production facility including the reactor 10 (stopping step S15). During the stop of the operation of the production facility, atmosphere enters the reaction system in the reactor 10 from outside in some cases.

Figure 2F:
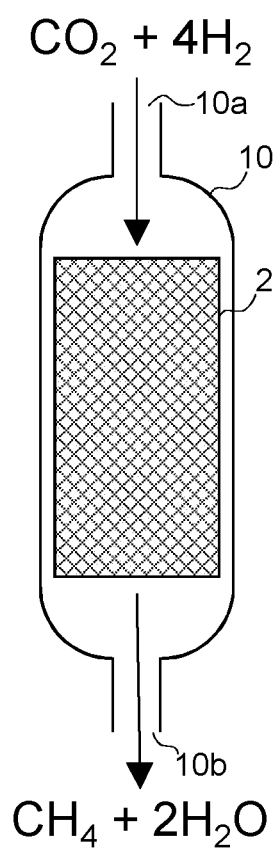
FIG. 2F is a process cross-sectional view illustrating the outline of the methane producing method according to the one embodiment.

Next, as illustrated in FIG. 1 and FIG. 2F, the raw material gas containing 20 volume % of carbon dioxide ($CO_2$) and 80 volume % of hydrogen ($H_2$) is supplied to the reactor via the gas inlet 10a. At this time, similarly to the first generating step, the heated raw material gas is supplied to the reactor 10. Accordingly, the methanation reaction occurs and methane is generated (second generating step S16).

As described above, in the methane producing method according to the one embodiment, after the first methanation reaction occurs to generate methane in the first generating step, before stopping the operation of the production facility including the reactor 10 in the stopping step, the oxygen gas in which the temperature and the oxygen concentration are controlled within the predetermined ranges is supplied to the reactor 10 to perform the heat treatment of the methanation catalyst 2 using the processing method for processing the methanation catalyst 2 according to one embodiment in the processing step (oxidizing step). Accordingly, the surface part of metallic nickel, in which nickel is present in the state of metal, contained in the methanation catalyst 2, is gradually oxidized, thereby forming the nickel oxide film. Therefore, even when the methanation catalyst 2 is exposed to the atmosphere entering to the reaction system in the reactor 10 from outside during the stop of the operation of the production facility, the oxidation reaction of metallic nickel by the high concentration of oxygen in the atmosphere is suppressed by the nickel oxide film covering the surface of metallic nickel. Accordingly, for example, even when the methanation catalyst 2 contacts the atmosphere in a high temperature state exceeding about 50° C., the occurrence of the rapid oxidation reaction of metallic nickel can be avoided. Consequently, the progress of the oxidation to the inside of the metallic nickel can be suppressed. Furthermore, the deterioration of the methanation catalyst 2 caused by the aggregation or the like of the carrier or nickel due to the heat generation by the rapid oxidation reaction of metallic nickel can be suppressed. Accordingly, the degradation of the catalyst performance of the methanation catalyst 2 can be suppressed.

Therefore, with the methanation catalyst processing method and the methane producing method according to the embodiment, the degradation of the catalyst performance of the methanation catalyst can be suppressed as described in the one embodiment.

Subsequently, the configurations of the methanation catalyst processing method, the methane producing method, and the methanation catalyst according to the embodiment will be described in detail.

1. Methanation Catalyst Processing Method

The methanation catalyst processing method according to the embodiment includes an oxidizing step of oxidizing nickel (Ni) through a heat treatment of a methanation catalyst by supplying an oxygen gas containing oxygen ($O_2$) to a reactor housing the methanation catalyst containing the nickel as a catalyst component. In the oxidizing step, the oxygen gas is supplied to the reactor such that the oxygen is supplied to 1 g of the methanation catalyst at a supply rate in a range of from 0.0213 mmol-$O_2$/sec·g-cat. to 0.0638 mmol-$O_2$/sec·g-cat., and a time period of the heat treatment of the methanation catalyst by supplying the oxygen gas to the reactor is set to 30 minutes or more.

While the methanation catalyst is not specifically limited insofar as the methanation catalyst contains nickel as a catalyst component, the methanation catalyst containing a carrier and nickel supported on the carrier is usually used. The carrier may be, for example, a porous carrier. As the material constituting the carrier, for example, ceria, silica, silica-alumina, titania, zirconia, ceria-zirconia, or the like may be used. While nickel as the catalyst component is not specifically limited insofar as the nickel is present as at least metallic nickel (metallic Ni) in the methanation catalyst as a target of the heat treatment in the oxidizing step, one present as metallic nickel and nickel oxide (NiO) may be used. The methanation catalyst may contain a component having a methanation catalytic activity as a catalyst component in addition to nickel. Nickel and the other catalyst components have, for example, particulate shapes.

While the weight ratio of the content of the nickel to the total content of the carrier and nickel in the methanation catalyst containing the carrier and nickel is not specifically limited, the weight ratio of the content of the nickel is, for example, in a range of from 20 weight % to 60 weight % in some embodiments, and may be in a range of from 30 weight % to 50 weight %. This is because the weight ratio equal to or more than the lower limit of the range provides a high methanation activity. That is, this is because active sites for causing the sufficient methanation reaction are obtained.

This is because the weight ratio equal to or less than the upper limit of the range ensures a specific surface area of the carrier component contributing to the dispersion of Ni particles, and the excessive growth of the Ni particles can be suppressed.

The method for oxidizing nickel through the heat treatment of the methanation catalyst by supplying the oxygen gas to the reactor is not specifically limited insofar as nickel can be oxidized by heating the methanation catalyst while flowing the oxygen gas around the methanation catalyst. Examples of the nickel oxidizing method include a method in which the oxygen gas is heated to make the oxygen gas temperature at the gas inlet of the reactor within a predetermined range described later, and the heated oxygen gas is flown around the methanation catalyst. Examples of the aspect of oxidizing nickel include an aspect in which the surface part of metallic nickel (metallic Ni) is oxidized to form a nickel oxide film containing nickel oxide (NiO).

The oxygen supply rate [mmol-$O_2$/sec·g-cat.] when the oxygen gas is supplied to the reactor means an amount of substance of oxygen supplied in 1 second for 1 g of the methanation catalyst when the oxygen gas is supplied to the reactor. The oxygen supply rate is not specifically limited insofar as the oxygen supply rate is within the range of from 0.0213 mmol-$O_2$/sec·g-cat. to 0.0638 mmol-$O_2$/sec·g-cat. This is because the oxygen supply rate equal to or more than the lower limits of these ranges enables the appropriate oxidation of metallic nickel so as to suppress the rapid oxidation reaction of metallic nickel in the atmospheric exposure. This is because the oxygen supply rate equal to or less than the upper limits of these ranges enables suppressing the excessive oxidation of metallic nickel that reduces the catalyst performance.

While the oxygen concentration of the oxygen gas is not specifically limited insofar as the oxygen supply rate is within the above-described range, the oxygen concentration of the oxygen gas is in a range of from 1 volume % to 3 volume % in some embodiments. This is because the oxygen concentration of the oxygen gas equal to or more than the lower limits of these ranges facilitates the appropriate oxidation of metallic nickel so as to suppress the rapid oxidation reaction of metallic nickel in the atmospheric exposure. This is because the oxygen concentration of the oxygen gas equal to or less than the upper limits of these ranges facilitates the suppression of the excessive oxidation of metallic nickel that reduces the catalyst performance.

While the flow rate of supplying the oxygen gas to the reactor is not specifically limited insofar as the oxygen supply rate is within the above-described range, the flow rate of the oxygen gas is in a range of from 3.33 L/minute to 30 L/minute in some embodiments. This is because the flow rate of the oxygen gas equal to or more than the lower limits of these ranges facilitates the appropriate oxidation of metallic nickel so as to suppress the rapid oxidation reaction of metallic nickel in the atmospheric exposure. This is because the flow rate of the oxygen gas equal to or less than the upper limits of these ranges facilitates the suppression of the excessive oxidation of metallic nickel that reduces the catalyst performance.

While the oxygen gas temperature at the gas inlet of the reactor is not specifically limited insofar as the oxygen supply rate is within the above-described range, the oxygen gas temperature at the gas inlet of the reactor is in a range of from 60° C. to 150° C. in some embodiments. This is because the oxygen gas temperature equal to or more than the lower limits of these ranges facilitates the appropriate oxidation of metallic nickel so as to suppress the rapid oxidation reaction of metallic nickel in the atmospheric exposure. This is because the oxygen gas temperature equal to or less than the upper limits of these ranges facilitates the suppression of the excessive oxidation of metallic nickel that reduces the catalyst performance.

While the pressure inside the reactor when the oxygen gas is supplied to the reactor is not specifically limited, the pressure inside the reactor is usually 1 atm (atmospheric pressure), and may be 1 atm or more.

The time period of the heat treatment of the methanation catalyst by supplying the oxygen gas to the reactor only needs to be 30 minutes or more. The time period of the heat treatment shorter than this range possibly fails to oxidize metallic nickel in the methanation catalyst. Meanwhile, in the time period of the heat treatment in this range, even when the time period of the heat treatment is lengthened, since the surface part of metallic nickel becomes nickel oxide and is stabilized, the excessive oxidation of metallic nickel is less likely to occur.

2. Methane Producing Method

The methane producing method according to the embodiment includes a processing step of oxidizing nickel through the heat treatment of the methanation catalyst housed in the reactor in the oxidizing step using the methanation catalyst processing method according to the embodiment, and a generating step of generating methane by supplying a raw material gas containing carbon dioxide ($CO_2$) and hydrogen ($H_2$) to the reactor housing the methanation catalyst in which the nickel has been oxidized in the processing step.

The methane generating method for generating the methane by supplying the raw material gas containing carbon dioxide and hydrogen to the reactor is not specifically limited insofar as methane can be generated through the methanation reaction by flowing the raw material gas around the methanation catalyst. For example, a process of generating methane through the methanation reaction by flowing the heated raw material gas around the methanation catalyst by supplying the heated raw material gas to the reactor may be used. Since the start temperature of the methanation reaction is about 150° C. or more, the heating temperature of the raw material gas in such a process is usually 150° C. or more.

While the raw material gas is not specifically limited insofar as carbon dioxide and hydrogen are contained, for example, a raw material gas containing 20 volume % of carbon dioxide and 80 volume % of hydrogen may be used. While the flow rate at which the raw material gas is supplied to the reactor is not specifically limited insofar as methane can be generated, for example, the flow rate of the raw material gas is in a range of from 0.070 L/minute to 0.400 L/minute relative to 1 g of the methanation catalyst in some embodiments. This is because the flow rate equal to or more than the lower limit of the range provides the sufficient methane generation amount per period, and the flow rate equal to or less than the upper limit of the range provides methane with the purity of methane at a sufficiently high level. While the pressure inside the reactor when the raw material gas is supplied to the reactor is not specifically limited, for example, the pressure inside the reactor is in a range of from 1 atm to 5 atm in some embodiments. This is because the pressure equal to or more than the lower limit of the range can avoid mixing of an atmospheric component into the reactor, and the pressure necessary for causing the sufficient methanation reaction is obtained. This is because the pressure equal to or less than the upper limits of these ranges can suppress the increase of energy necessary for applying pressure and suppress the decrease in energy efficiency in the methanation, and can reduce the facility introduction cost without introducing a facility for high pressure.

The methane producing method is not specifically limited insofar as the methane producing method is a producing method as described above. However, when the temperature [° C.] of the oxygen gas at the gas inlet of the reactor in the oxidizing step is X1, the oxygen concentration [volume %] of the oxygen gas in the oxidizing step is X2, and the temperature [° C.] of the raw material gas at the gas inlet of the reactor when the conversion rate of the carbon dioxide in the generating step is 50% is Y, a method in which the following formulae (1) to (4) are satisfied may be employed. By setting the temperature X1 and the concentration X2 such that the temperature Y becomes less than 250° C., the methanation reaction can be progressed with the methanation catalyst in which the excessive oxidation of metallic nickel that reduces the catalyst performance is suppressed. Furthermore, the operation temperature of the methanation reaction can be decreased to a low temperature, thereby enabling the reduction of the energy consumption. By setting the temperature X1 and the concentration X2 such that the temperature Y becomes 160° C. or more, the methanation reaction can be progressed with the methanation catalyst in which metallic nickel is oxidized.

$$Y=153.091+0.487X1+17.714X2 \quad (1)$$

$$160 \le Y < 250 \quad (2)$$

$$0 < X1 \quad (3)$$

$$0 < X2 \quad (4)$$

The method for obtaining the raw material gas temperature Y at the gas inlet of the reactor when the conversion rate of the carbon dioxide becomes 50% in the generating step is, for example, as follows. In the generating step, in a process of increasing the temperature of the raw material gas at the gas inlet of the reactor, for example, from 150° C. to 400° C., the carbon dioxide concentration [volume %] of an outflow gas at the gas outlet of the reactor is measured. Next, for each temperature of the raw material gas at the gas inlet, the conversion rate of the carbon dioxide is calculated from the carbon dioxide concentration [volume %] of the raw material gas and the carbon dioxide concentration of the outflow gas. Next, based on the calculation result, the change of the conversion rate of the carbon dioxide relative to the temperature of the raw material gas at the gas inlet is obtained, and the temperature Y is acquired from the content of the change of the conversion rate.

3. Methanation Catalyst

The methanation catalyst according to the embodiment is a methanation catalyst containing nickel as a catalyst component. The nickel is present as metallic nickel (metallic Ni) and nickel oxide (NiO). The weight ratio of the content of the metallic nickel to the total content of the metallic nickel and the nickel oxide is in a range of from 58 weight % to 67 weight %. This is because the weight ratio of the metallic nickel equal to or more than the lower limit of the range ensures the sufficient catalyst performance. This is because the weight ratio of the metallic nickel equal to or less than the upper limits of these ranges can maintain the sufficient catalyst performance by suppressing the rapid oxidation reaction of metallic nickel by the nickel oxide film covering the surface of metallic nickel in the atmospheric exposure of the methanation catalyst.

While the methanation catalyst is not specifically limited, the methanation catalyst is, for example, a methanation catalyst, in which nickel is oxidized, produced by oxidizing nickel through the heat treatment of the methanation catalyst housed in the reactor in the oxidizing step using the methanation catalyst processing method according to the embodiment.

EXAMPLE

The following further specifically describes the methanation catalyst processing method, the methane producing method, and the methanation catalyst according to the embodiment of the present disclosure with Examples and Comparative Examples.

Example 1

Figure 3:
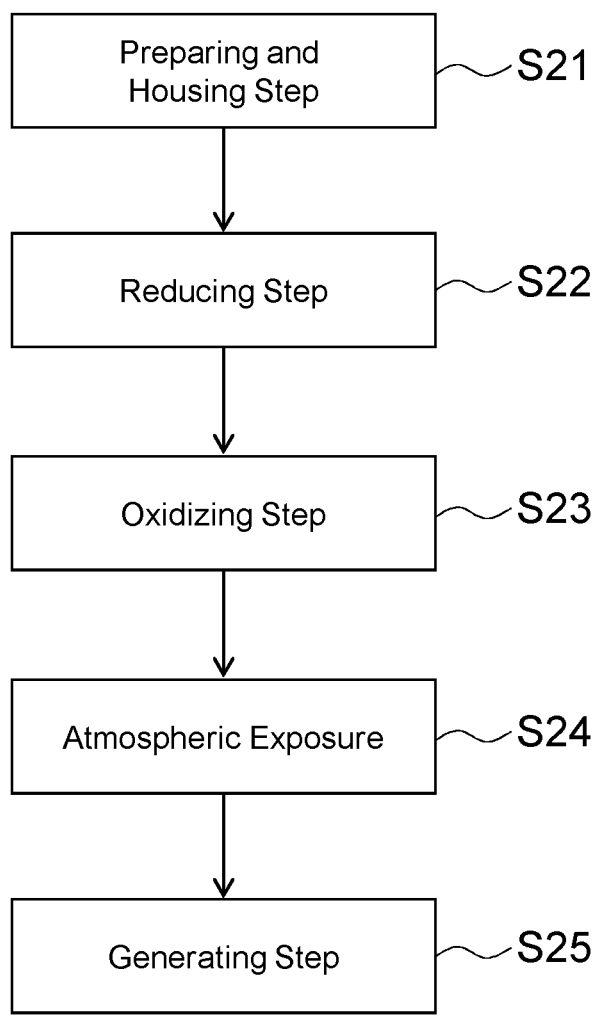
FIG. 3 is a flowchart illustrating the operation process of the experiment of performing the methane producing method of Example 1.
Figure 4:
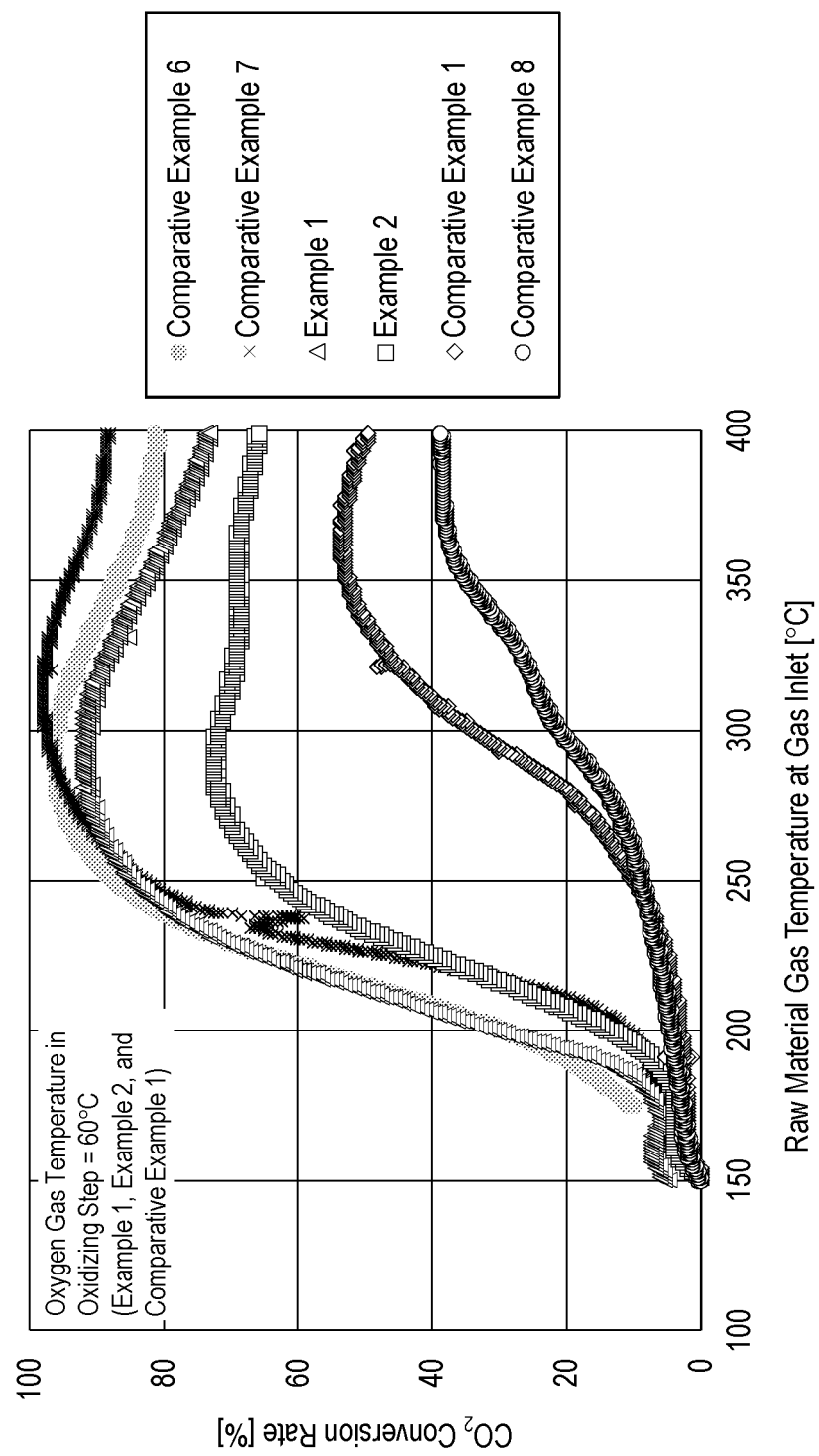
FIG. 4 is a graph illustrating changes of the conversion rate of the carbon dioxide relative to the temperature of the raw material gas at the gas inlet in Example 1, Example 2, and Comparative Example 1.
Figure 5:
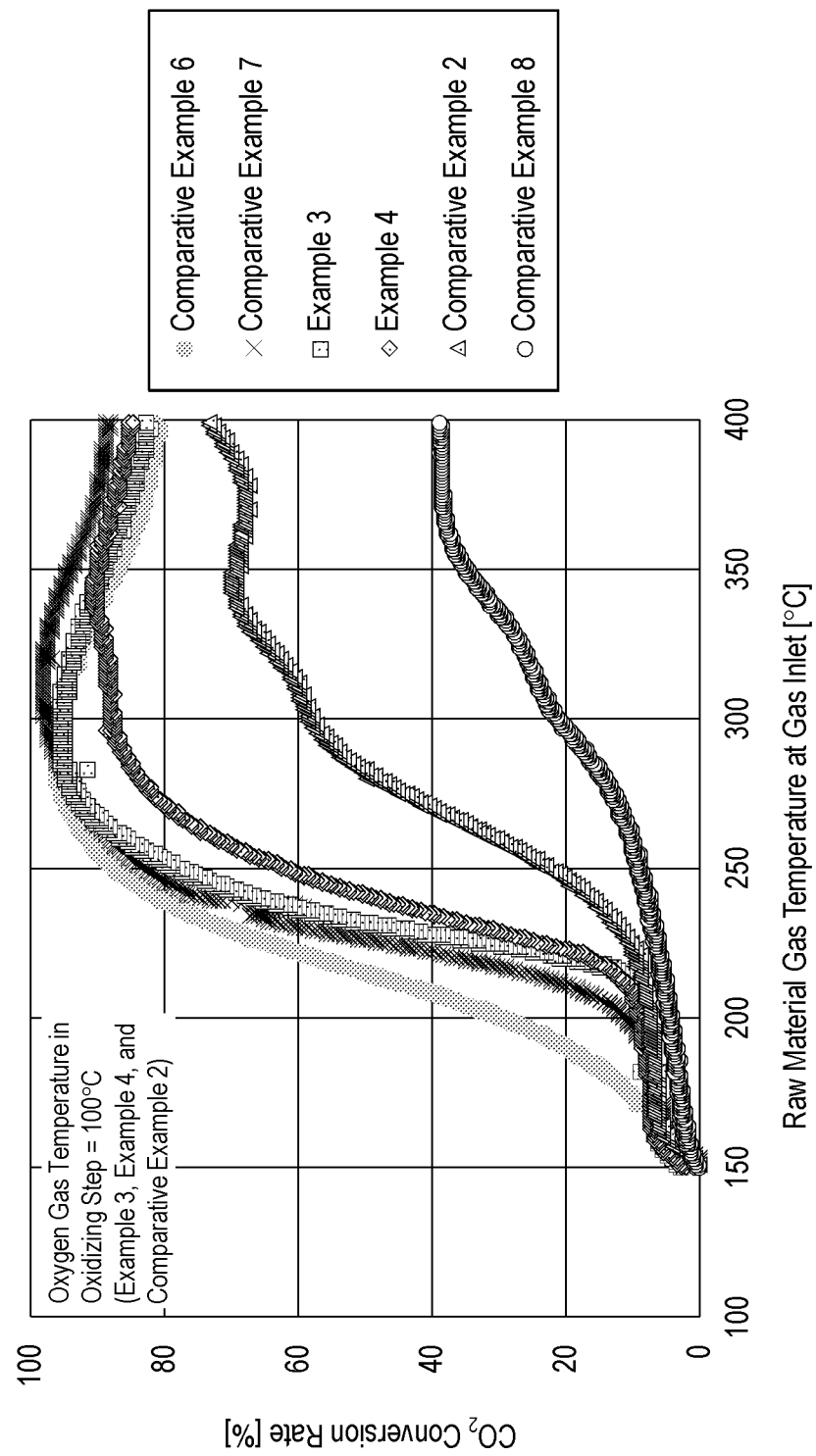
FIG. 5 is a graph illustrating changes of the conversion rate of the carbon dioxide relative to the temperature of the raw material gas at the gas inlet in Example 3, Example 4, and Comparative Example 2.
Figure 6:
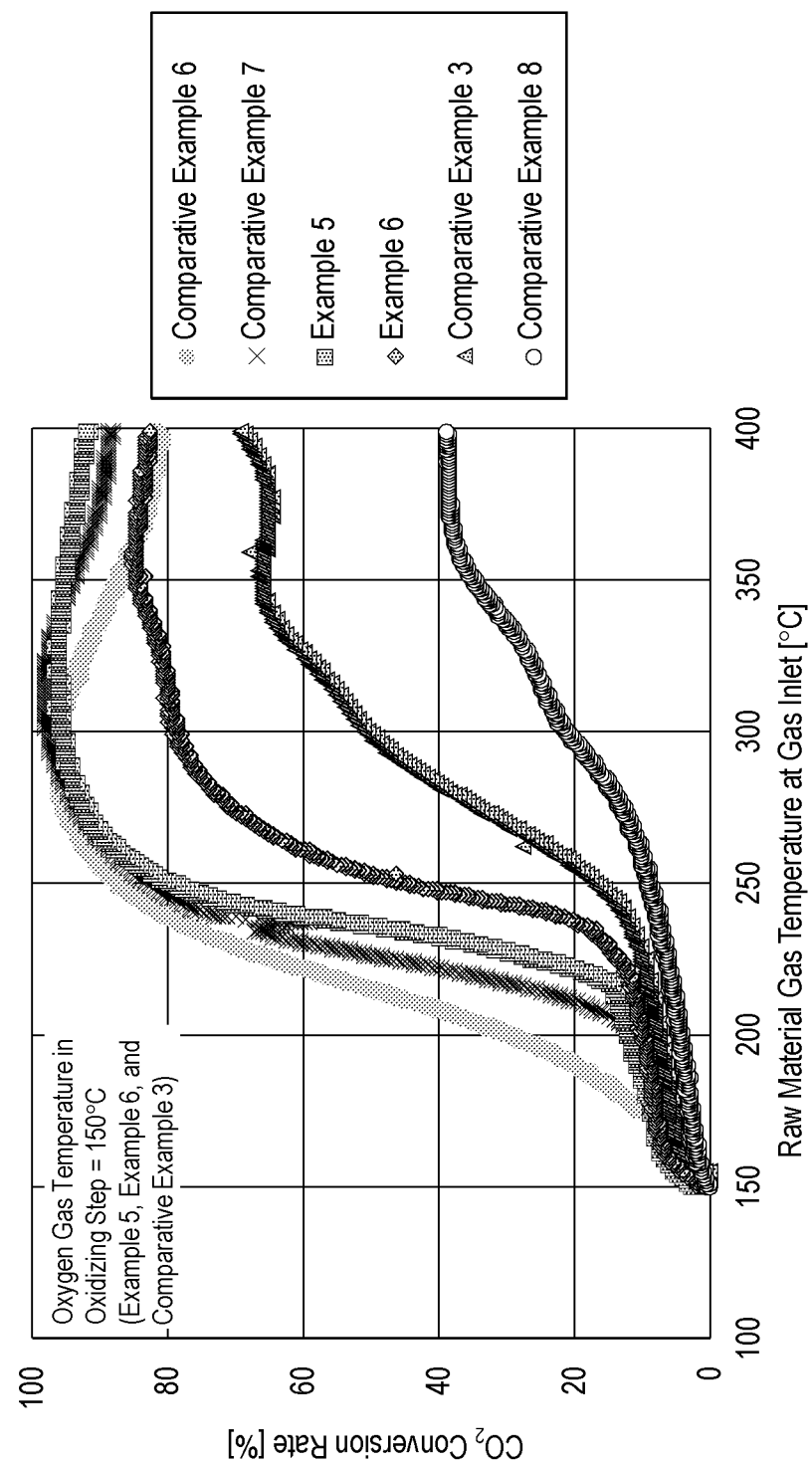
FIG. 6 is a graph illustrating changes of the conversion rate of the carbon dioxide relative to the temperature of the raw material gas at the gas inlet in Example 5, Example 6, and Comparative Example 3.
Figure 7:
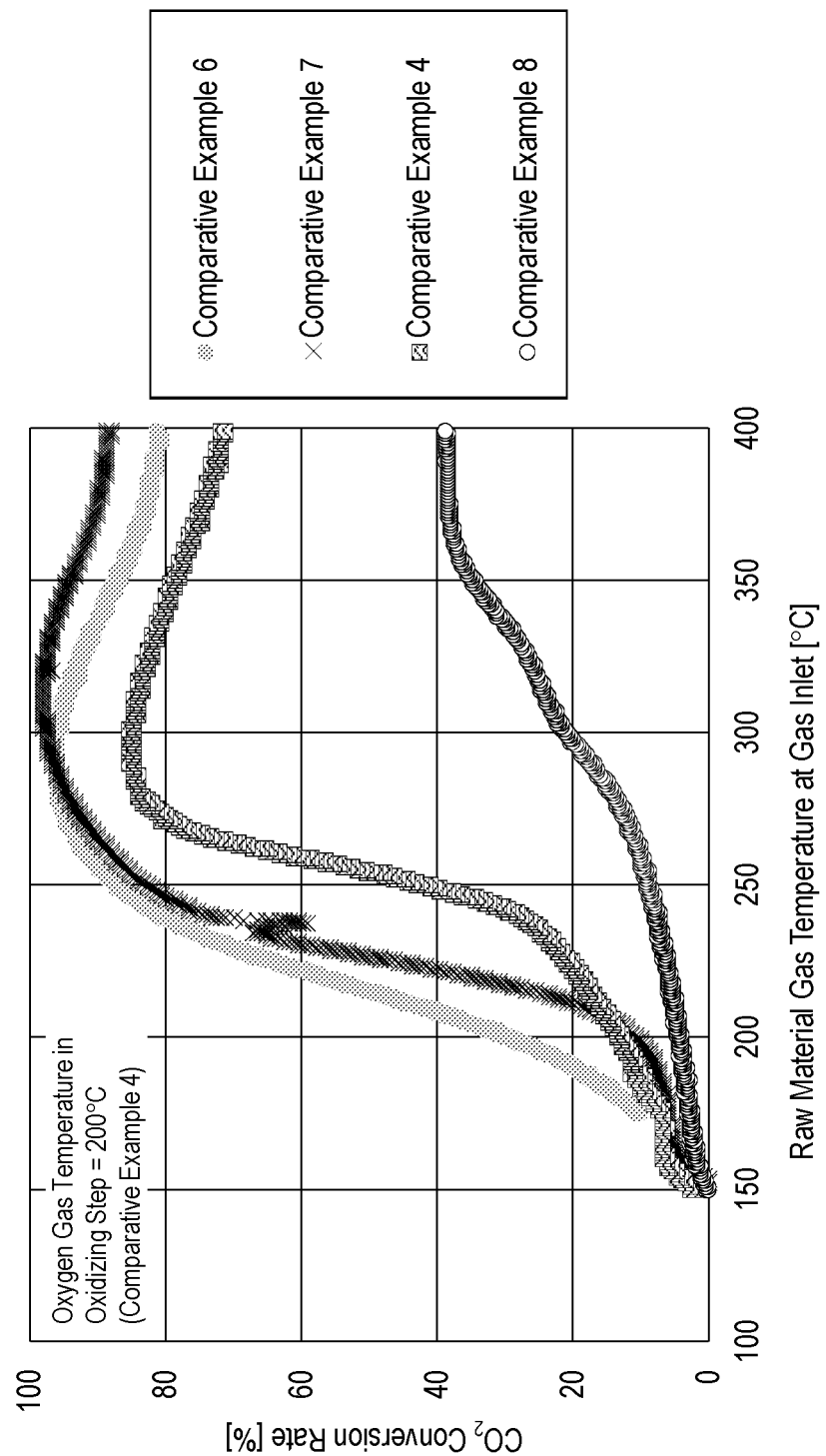
FIG. 7 is a graph illustrating a change of the conversion rate of the carbon dioxide relative to the temperature of the raw material gas at the gas inlet in Comparative Example 4.
Figure 8:
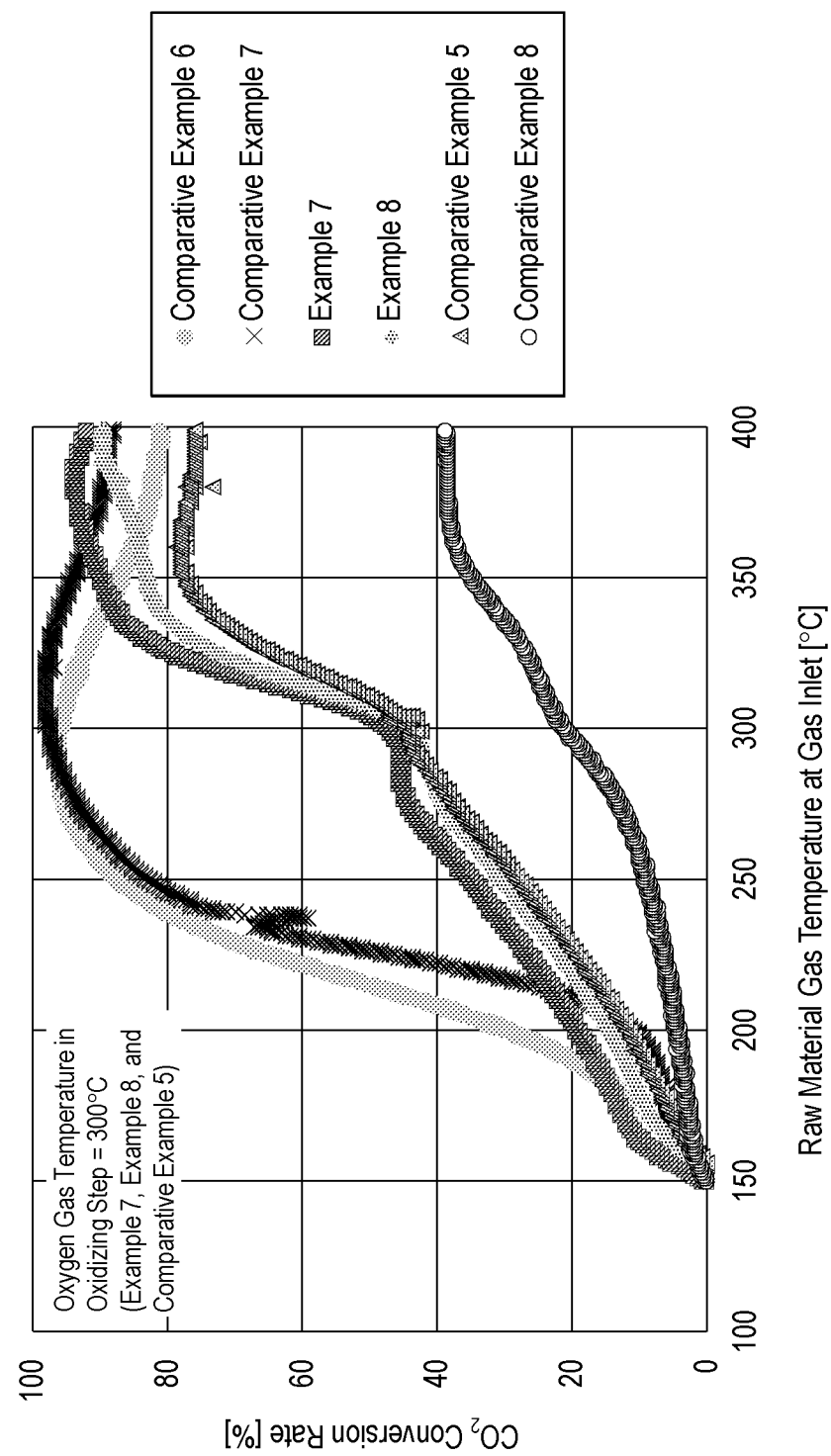
FIG. 8 is a graph illustrating changes of the conversion rate of the carbon dioxide relative to the temperature of the raw material gas at the gas inlet in Example 7, Example 8, and Comparative Example 5.
Figure 9:
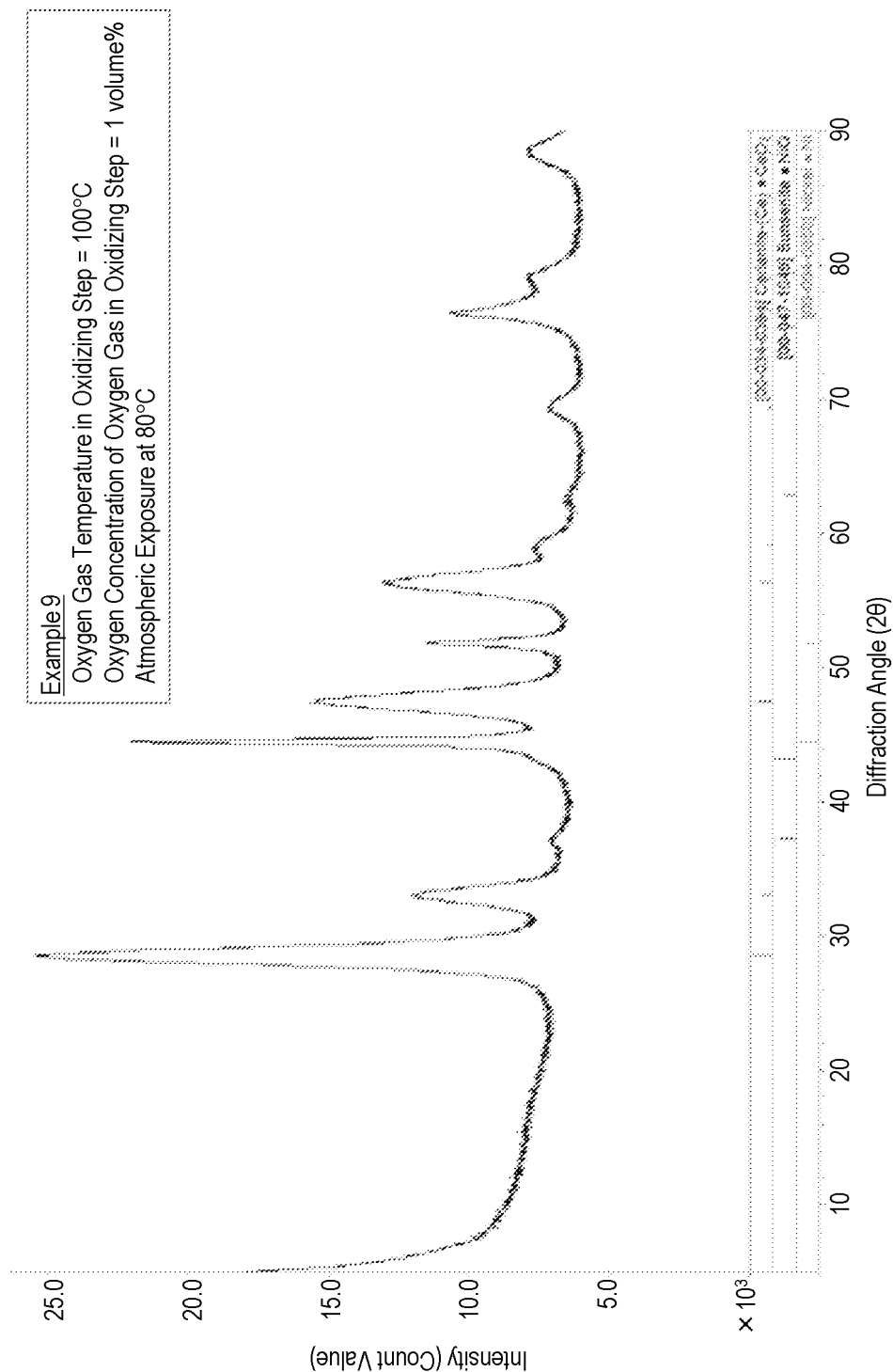
FIG. 9 is an X-ray diffraction pattern of the methanation catalyst after the atmospheric exposure in the experiment of Example 9.
Figure 10:
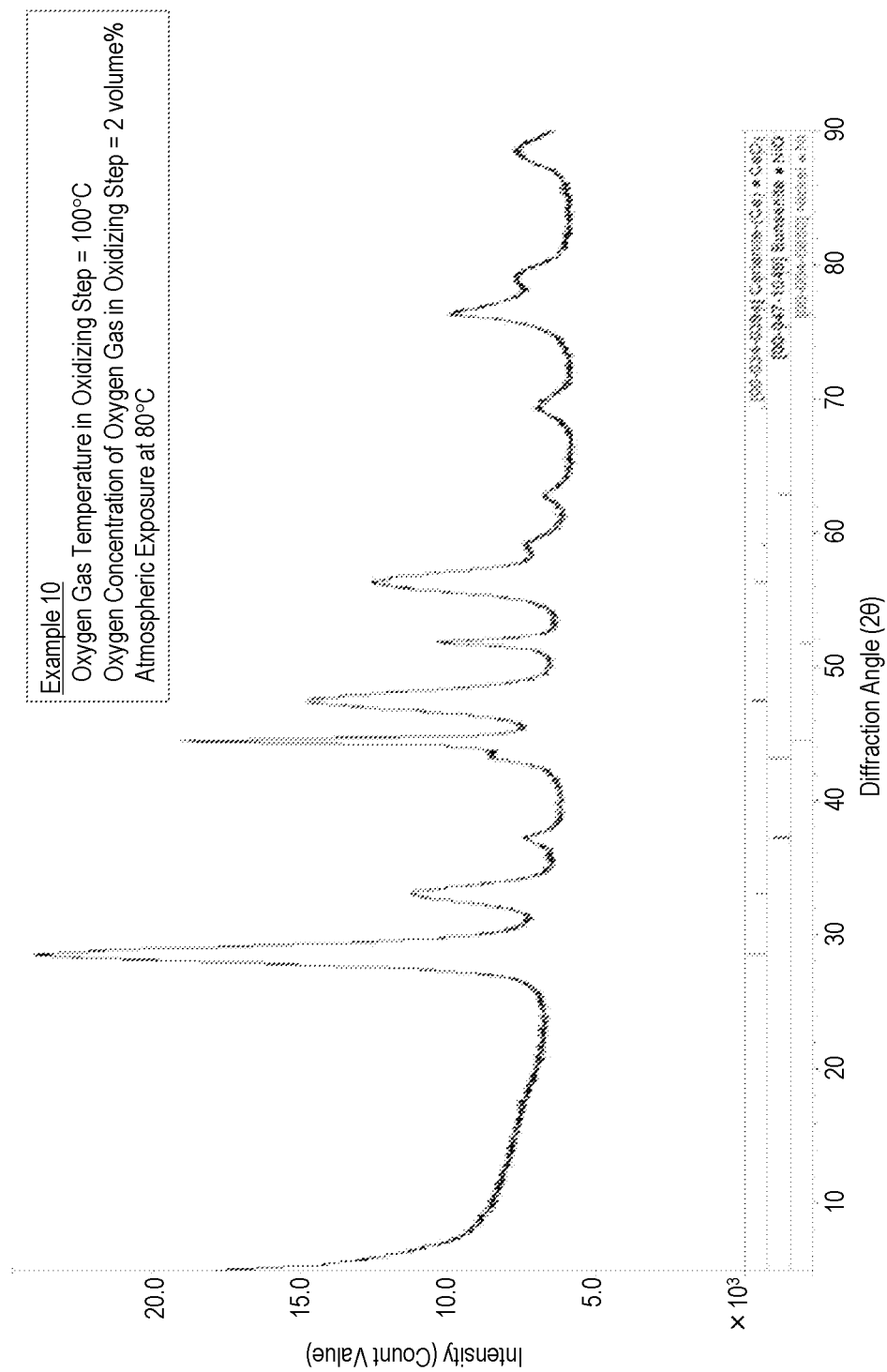
FIG. 10 is an X-ray diffraction pattern of the methanation catalyst after the atmospheric exposure in the experiment of Example 10.
Figure 11:
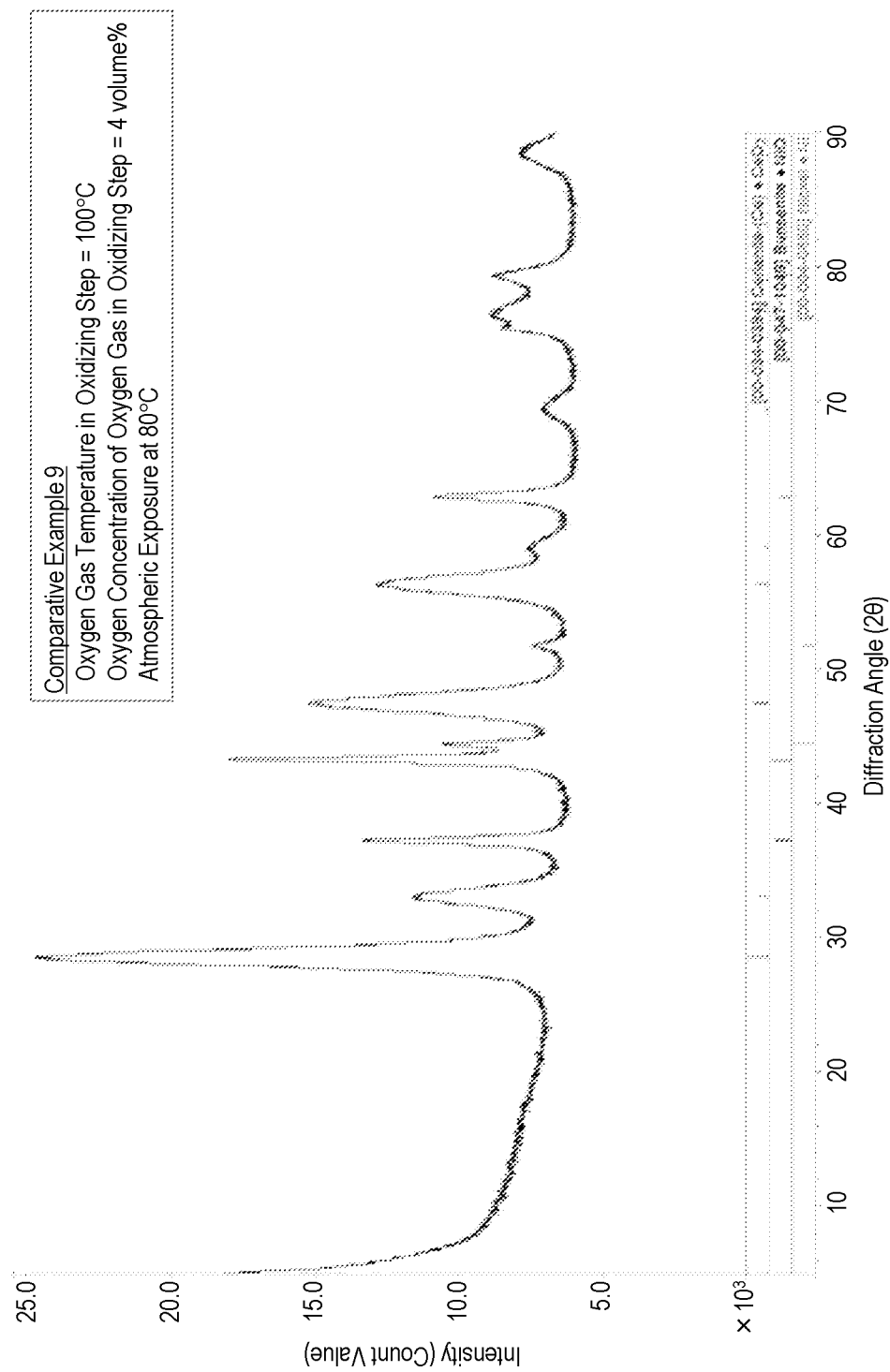
FIG. 11 is an X-ray diffraction pattern of the methanation catalyst after the atmospheric exposure in the experiment of Comparative Example 9.
Figure 12:
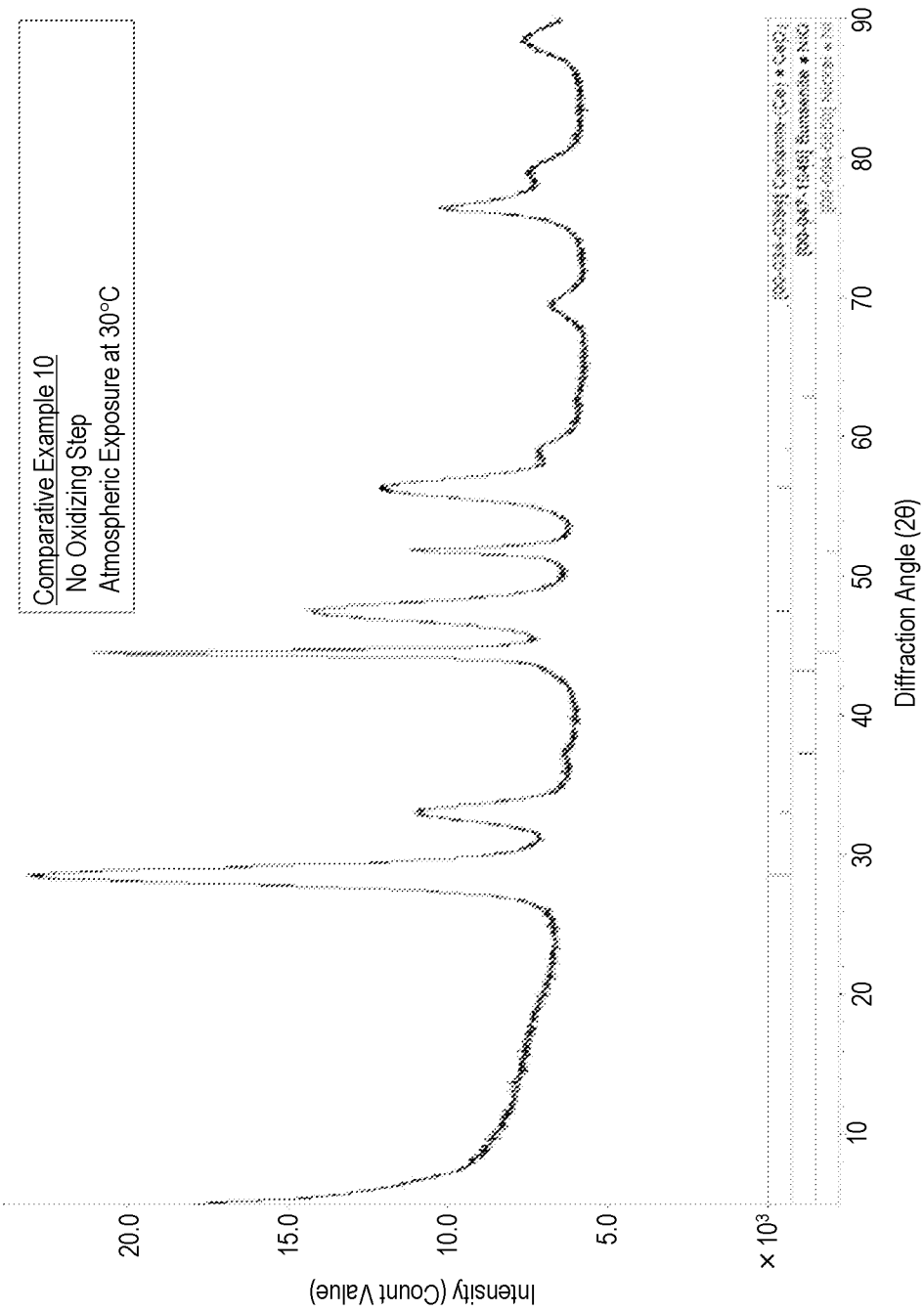
FIG. 12 is an X-ray diffraction pattern of the methanation catalyst after the atmospheric exposure in the experiment of Comparative Example 10.

An experiment of performing the methane producing method according to the embodiment was conducted. FIG. 3 is a flowchart illustrating the operation process of the experiment of performing the methane producing method of Example 1.

In the experiment, first, as illustrated in FIG. 3, as the methanation catalyst containing nickel (Ni) as a catalyst component, a methanation catalyst containing a carrier containing ceria ($CeO_2$) and nickel supported on the carrier was prepared, and the methanation catalyst was housed in a reactor in a methane production facility (preparing and housing step S21). In the prepared methanation catalyst, the weight ratio of the content of the nickel to the total content of ceria and nickel is 39 weight %, and the weight of the prepared methanation catalyst is 3.5 g. Since the prepared methanation catalyst is sintered under an oxygen atmosphere in the synthesis, nickel is present as not only metallic nickel (metallic Ni) but also nickel oxide (NiO).

Next, as illustrated in FIG. 3, a reducing gas containing 20 volume % of hydrogen ($H_2$) and 80 volume % of nitrogen ($N_2$) at 400° C. was supplied to the reactor via a gas inlet, thereby flowing the reducing gas around the methanation catalyst. Accordingly, nickel oxide in the methanation catalyst was reduced to metallic nickel (reducing step S22).

Next, as illustrated in FIG. 3, after ending the reducing step by stopping the supply of the reducing gas to the reactor, in a state where the methanation catalyst was not extracted from the reactor and left, the temperature of the methanation catalyst was decreased to equal to or less than a temperature of an oxygen gas at a gas inlet of the reactor in a later oxidizing step, and subsequently, the oxygen gas containing oxygen and nitrogen was supplied to the reactor via the gas inlet, thereby flowing the oxygen gas around the methanation catalyst to perform the heat treatment of the methanation catalyst. At this time, as illustrated in Table 1 below, the oxygen gas temperature at the gas inlet of the reactor was adjusted to 60° C. by heating the oxygen gas. Subsequently, by adjusting the oxygen concentration of the oxygen gas to 2 volume %, and adjusting the flow rate at which the oxygen gas is supplied to the reactor to 10 L/minute, the oxygen gas was supplied to the reactor such that the oxygen was supplied to 1 g of the methanation catalyst at the supply rate of 0.0425 mmol-$O_2$/sec·g-cat. 10 L/minute of the oxygen gas flow rate is SV=188679 $h^{-1}$ in the conversion into a space velocity SV calculated by dividing the oxygen gas flow rate by the volume of the methanation catalyst. The pressure inside the reactor was set to 1 atm (atmospheric pressure). Furthermore, the time period for performing the heat treatment of the methanation catalyst by supplying the oxygen gas to the reactor was set to 30 minutes. By thus oxidizing a surface part of metallic nickel through the heat treatment of the methanation catalyst, a nickel oxide film containing nickel oxide (NiO) was formed (oxidizing step S23).

Next, as illustrated in FIG. 3, after the oxidizing step was ended by stopping the supply of the oxygen gas to the reactor, the methanation catalyst was extracted from the reactor to outside of the reactor and exposed to the atmosphere when the temperature of the methanation catalyst inside the reactor was decreased to 80° C., and left until the temperature of the methanation catalyst was decreased to ordinary temperature (atmospheric exposure S24).

Next, as illustrated in FIG. 3, after the atmospherically exposed methanation catalyst was housed in the reactor again, the raw material gas containing 20 volume % of carbon dioxide ($CO_2$) and 80 volume % of hydrogen ($H_2$) was supplied to the reactor via the gas inlet. At this time, the flow rate of the raw material gas was set to 0.530 L/minute (space velocity SV=10000 $h^{-1}$), and the pressure inside the reactor was set to 3 atm. While increasing the temperature of the raw material gas at the gas inlet of the reactor from 150° C. to 400° C. by heating the raw material gas, the heated raw material gas was supplied to the reactor. Accordingly, the heated raw material gas was flown around the methanation catalyst to cause the methanation reaction, thereby generating methane (generating step S25). The experiment of performing the methane producing method was conducted as described above.

Example 2

As illustrated in Table 1 below, the experiment of performing the methane producing method was conducted similarly to Example 1 except that the oxygen supply rate was changed to 0.0638 mmol-$O_2$/sec·g-cat. by changing the oxygen concentration of the oxygen gas to 3 volume % in the oxidizing step.

Comparative Example 1

As illustrated in Table 1 below, the experiment of performing the methane producing method was conducted similarly to Example 1 except that the oxygen supply rate was changed to 0.2126 mmol-$O_2$/sec·g-cat. by changing the oxygen concentration of the oxygen gas to 10 volume % in the oxidizing step.

Example 3

As illustrated in Table 1 below, the experiment of performing the methane producing method was conducted similarly to Example 1 except that the oxygen gas temperature at the gas inlet of the reactor was changed to 100° C., and the oxygen supply rate was changed to 0.0213 mmol-$O_2$/sec·g-cat. by changing the oxygen concentration of the oxygen gas to 1 volume % in the oxidizing step.

Example 4

As illustrated in Table 1 below, the experiment of performing the methane producing method was conducted similarly to Example 3 except that the oxygen supply rate was changed to 0.0425 mmol-$O_2$/sec·g-cat. by changing the oxygen concentration of the oxygen gas to 2 volume % in the oxidizing step.

Comparative Example 2

As illustrated in Table 1 below, the experiment of performing the methane producing method was conducted similarly to Example 3 except that the oxygen supply rate was changed to 0.0850 mmol-$O_2$/sec·g-cat. by changing the oxygen concentration of the oxygen gas to 4 volume % in the oxidizing step.

Example 5

As illustrated in Table 1 below, the experiment of performing the methane producing method was conducted similarly to Example 1 except that the oxygen gas temperature at the gas inlet of the reactor was changed to 150° C., and the oxygen supply rate was changed to 0.0213 mmol-$O_2$/sec·g-cat. by changing the oxygen concentration of the oxygen gas to 1 volume % in the oxidizing step.

Example 6

As illustrated in Table 1 below, the experiment of performing the methane producing method was conducted similarly to Example 5 except that the oxygen supply rate was changed to 0.0425 mmol-$O_2$/sec·g-cat. by changing the oxygen concentration of the oxygen gas to 2 volume % in the oxidizing step.

Comparative Example 3

As illustrated in Table 1 below, the experiment of performing the methane producing method was conducted similarly to Example 5 except that the oxygen supply rate was changed to 0.0850 mmol-$O_2$/sec·g-cat. by changing the oxygen concentration of the oxygen gas to 4 volume % in the oxidizing step.

Comparative Example 4

As illustrated in Table 1 below, the experiment of performing the methane producing method was conducted similarly to Example 1 except that the oxygen gas temperature at the gas inlet of the reactor was changed to 200° C., and the oxygen supply rate was changed to 0.0021 mmol-$O_2$/sec·g-cat. by changing the oxygen concentration of the oxygen gas to 0.1 volume % in the oxidizing step.

Example 7

As illustrated in Table 1 below, the experiment of performing the methane producing method was conducted similarly to Example 1 except that the oxygen gas temperature at the gas inlet of the reactor was changed to 300° C., and the oxygen supply rate was changed to 0.0213 mmol-$O_2$/sec·g-cat. by changing the oxygen concentration of the oxygen gas to 1 volume % in the oxidizing step.

Example 8

As illustrated in Table 1 below, the experiment of performing the methane producing method was conducted similarly to Example 7 except that the oxygen supply rate was changed to 0.0425 mmol-$O_2$/sec·g-cat. by changing the oxygen concentration of the oxygen gas to 2 volume % in the oxidizing step.

Comparative Example 5

As illustrated in Table 1 below, the experiment of performing the methane producing method was conducted similarly to Example 7 except that the oxygen supply rate was changed to 0.0850 mmol-O₂/sec·g-cat. by changing the oxygen concentration of the oxygen gas to 4 volume % in the oxidizing step.

Comparative Example 6

As illustrated in Table 1 below, after ending the reducing step, the temperature of the methanation catalyst was decreased to an initial temperature (150° C.) of the raw material gas at the gas inlet of the reactor in the later generating step in a state where the methanation catalyst was not extracted from the reactor to be left without performing the oxidizing step and the atmospheric exposure. Subsequently, the raw material gas was supplied to the reactor via the gas inlet to flow the raw material gas around the methanation catalyst, thereby causing the methanation reaction to generate methane (generating step). The experiment of performing the methane producing method was conducted similarly to Example 1 except these points.

Comparative Example 7

As illustrated in Table 1 below, after ending the reducing step, the methanation catalyst was extracted from the reactor to outside of the reactor and exposed to the atmosphere when the temperature of the methanation catalyst inside the reactor was decreased to 30° C. without performing the oxidizing step, and the methanation catalyst was left in the atmosphere (atmospheric exposure). Subsequently, after the atmospherically exposed methanation catalyst was housed in the reactor again, the raw material gas was supplied to the reactor via the gas inlet to flow the raw material gas around the methanation catalyst, thereby causing the methanation reaction to generate methane (generating step). The experiment of performing the methane producing method was conducted similarly to Example 1 except these points.

Comparative Example 8

As illustrated in Table 1 below, the experiment of performing the methane producing method was conducted similarly to Comparative Example 7 except that the methanation catalyst was extracted from the reactor to outside of the reactor and exposed to the atmosphere when the temperature of the methanation catalyst inside the reactor was decreased to 60° C. in the atmospheric exposure.

TABLE 1

| | | Conditions in Oxidizing Step | | | | | | |
|---|---|---|---|---|---|---|---|---|
| | Oxidizing Step Performed | Oxygen Gas Temperature [° C.] | Oxygen Concentration of Oxygen Gas [Volume %] | Oxygen Gas Flow Rate [L/min] | Oxygen Supply Rate [mmol-O₂/ sec · g-cat.] | Pressure inside Reactor [atm] | Oxygen Supply Period (Heat Treatment Period) | Atmospheric Exposure Performed | Catalyst Temperature in Atmospheric Exposure [° C.] |
| Example 1 | Yes | 60 | 2 | 10 | 0.0425 | 1 | 30 | Yes | 80 |
| Example 2 | Yes | 60 | 3 | 10 | 0.0638 | 1 | 30 | Yes | 80 |
| Comparative Example 1 | Yes | 60 | 10 | 10 | 0.2126 | 1 | 30 | Yes | 80 |
| Example 3 | Yes | 100 | 1 | 10 | 0.0213 | 1 | 30 | Yes | 80 |
| Example 4 | Yes | 100 | 2 | 10 | 0.0425 | 1 | 30 | Yes | 80 |
| Comparative Example 2 | Yes | 100 | 4 | 10 | 0.0850 | 1 | 30 | Yes | 80 |
| Example 5 | Yes | 150 | 1 | 10 | 0.0213 | 1 | 30 | Yes | 80 |
| Example 6 | Yes | 150 | 2 | 10 | 0.0425 | 1 | 30 | Yes | 80 |
| Comparative Example 3 | Yes | 150 | 4 | 10 | 0.0850 | 1 | 30 | Yes | 80 |
| Comparative Example 4 | Yes | 200 | 0.1 | 10 | 0.0021 | 1 | 30 | Yes | 80 |
| Example 7 | Yes | 300 | 1 | 10 | 0.0213 | 1 | 30 | Yes | 80 |
| Example 8 | Yes | 300 | 2 | 10 | 0.0425 | 1 | 30 | Yes | 80 |
| Comparative Example 5 | Yes | 300 | 4 | 10 | 0.0850 | 1 | 30 | Yes | 80 |
| Comparative Example 6 | No | — | — | — | — | — | — | No | — |
| Comparative Example 7 | No | — | — | — | — | — | — | Yes | 30 |
| Comparative Example 8 | No | — | — | — | — | — | — | Yes | 60 |

* Underlined parts indicate that values are out of ranges of conditions of the present disclosure.

[Temperature Change of Methanation Catalyst in Atmospheric Exposure]

The temperature changes of the methanation catalyst in the atmospheric exposure in the experiments of Examples 1 to 8 and Comparative Examples 1 to 5, 7, and 8 were evaluated. Specifically, in each of the experiments of examples, the surface temperature of the methanation catalyst was measured by an infrared temperature sensor while the methanation catalyst was left after being extracted from the reactor to outside of the reactor and exposed to the atmosphere. As a result, rise of the surface temperature of the methanation catalyst was not confirmed in the atmospheric exposure of the methanation catalyst in the experiments of Examples 1 to 8 and Comparative Examples 1 to 5. The reason is considered that the surface part of metallic nickel contained in the methanation catalyst was oxidized and the nickel oxide film was formed in the oxidizing step, a stable state was provided thereby, and the rapid oxidation reaction of the metallic nickel was avoided in the atmospheric exposure. Furthermore, in the atmospheric exposure of the methanation catalyst in the experiment of Comparative Example 7, the rise of the surface temperature of the methanation catalyst was not confirmed. The reason is considered that the temperature in the atmospheric exposure is low. On the other hand, the rapid rise of the surface temperature of the methanation catalyst was confirmed in the atmospheric exposure of the methanation catalyst in the experiment of Comparative Example 8. The reason is considered that the temperature in the atmospheric exposure is high.

[Change of Conversion Rate of Carbon Dioxide Relative to Temperature of Raw Material Gas at Gas Inlet of Reactor]

The changes of the conversion rate of the carbon dioxide relative to the temperature of the raw material gas at the gas inlet of the reactor in the generating step were evaluated for the experiments of Examples 1 to 8 and Comparative Examples 1 to 8. Specifically, in the generating step in each of the experiments of examples, the carbon dioxide concentration [volume %] and the methane concentration [volume %] of the outflow gas at the gas outlet of the reactor were measured by a gas chromatography in the process of increasing the temperature of the raw material gas at the gas inlet of the reactor from 150° C. to 400° C. Subsequently, for each temperature of the raw material gas at the gas inlet, the conversion rate of the carbon dioxide [%](=(carbon dioxide concentration of raw material gas−carbon dioxide concentration of outflow gas)/carbon dioxide concentration of raw material gas×100) was calculated from the carbon dioxide concentration of the raw material gas and the carbon dioxide concentration of the outflow gas.

Based on the calculation result of the conversion rate of the carbon dioxide at each temperature of the raw material gas at the gas inlet in Examples 1 to 8 and Comparative Examples 1 to 8, the change of the conversion rate of the carbon dioxide relative to the temperature of the raw material gas at the gas inlet was obtained. FIG. 4 to FIG. 8 are graphs illustrating changes of the conversion rate of the carbon dioxide relative to the temperature of the raw material gas at the gas inlet in Examples 1 to 8 and Comparative Examples 1 to 8. By collating the conditions in the oxidizing step indicated in the Table 1 and the graphs illustrated in FIG. 4 to FIG. 8, it is found that there is a difference in catalyst performance of the methanation catalyst depending on the temperature and the oxygen concentration of the oxygen gas in the oxidizing step. Additionally, it is indicated that for the conditions in the oxidizing step, there are ranges capable of maintaining the catalyst performance of the methanation catalyst regardless of the atmospheric exposure of the methanation catalyst.

While it is necessary to apply heat to the methanation catalyst from outside for the sufficient progress of the catalytic reaction, since the methanation reaction is an exothermic reaction, when the conversion rate of the carbon dioxide reaches about 50%, the methanation catalyst is heated by the heat of reaction in the methanation reaction, and the conversion rate of the carbon dioxide reaches the maximum conversion rate. From this reason, the temperature Y [° C.] of the raw material gas at the gas inlet of the reactor when the conversion rate of the carbon dioxide in the generating step becomes 50% is important, and the temperature Y is an indicator for determining the qualities under the conditions in the oxidizing step. Therefore, from the changes of the conversion rate of the carbon dioxide relative to the temperature Y of the raw material gas at the gas inlet in Examples 1 to 8 and Comparative Examples 1 to 8, the temperature Y of the raw material gas at the gas inlet of the reactor when the conversion rate of the carbon dioxide became 50% was obtained for each of the examples. Based on the results, Table 2 below indicates the raw material gas temperature Y at the gas inlet of the reactor when the conversion rate of the carbon dioxide becomes 50% in the generating step relative to the oxygen gas temperature X1 at the gas inlet of the reactor and the oxygen concentration X2 of the oxygen gas in the oxidizing step. In Table 2 below, "Good" representing that the temperature X1 and the concentration X2 provide a good condition is indicated in parentheses when the temperature Y is less than 250° C., and "Poor" representing that the temperature X1 and the concentration X2 provide a poor condition is indicated in parentheses when the temperature Y is equal to or more than 250° C. The reason why the threshold of the temperature Y was set to 250° C. and the case where the temperature Y was less than 250° C. was determined as the good condition includes, for example, that: 1) the lower the operation temperature of the methanation reaction is, the better it is (higher temperature increases energy consumption); 2) the methanation catalyst temperature at 350° C. or more causes a reverse reaction of the methanation reaction, thus possibly suppressing the reactivity of the methanation reaction, and the temperature Y at less than 250° C. facilitates decreasing the methanation catalyst temperature to less than 350° C.

TABLE 2

Raw Material Gas Temperature Y When Carbon Dioxide Conversion Rate Becomes 50% in Generating Step Relative to Oxygen Gas Temperature X1 and Oxygen Concentration X2 of Oxygen Gas in Oxidizing Step

| | | Oxygen Concentration X2 of Oxygen Gas in Oxidizing Step [Volume %] | | | | | |
|---|---|---|---|---|---|---|---|
| | | 0.1 | 1 | 2 | 3 | 4 | 10 |
| Oxygen Gas Temperature X1 in Oxidizing Step [° C.] | 300 | — | [305 (Poor)] | [308 (Poor)] | — | [310 (Poor)] | — |
| | 200 | 254 (Poor) | — | — | — | — | — |
| | 150 | — | 236 (Good) | 253 (Poor) | — | 299 (Poor) | — |
| | 100 | — | 232 (Good) | 241 (Good) | — | 282 (Poor) | — |
| | 60 | — | — | 213 (Good) | 233 (Good) | — | [337 (Poor)] |

* 1 "Good" in parentheses means a good condition under which the temperature Y is less than 250° C., and "Poor" in parentheses means a poor condition under which the temperature Y is 250° C. or more.
* 2 The regression formula representing the relation between the objective variable (Y) and the explanatory variables (X1 and X2) was derived using the data excluding the data in the brackets [ ].

Furthermore, it was attempted to generalize the relation between the temperature X1 of the oxygen gas at the gas inlet of the reactor and the oxygen concentration X2 of the oxygen gas in the oxidizing step in which the temperature Y of the raw material gas at the gas inlet of the reactor became less than 250° C. when the conversion rate of the carbon dioxide in the generating step was 50%. Specifically, using the temperature Y [° C.] as an objective variable, and the temperature X1 [° C.] and the concentration X2 [volume %] as explanatory variables, a multiple regression analysis was performed with data excluding data in the brackets [ ] among a plurality of data sets of Y, X1, and X2 indicated in the Table 2, thereby deriving a formula (1) below as a regression formula representing the relation between the objective variable (Y) and the explanatory variables (X1 and X2). The reason why the data in the brackets H among the plurality of pieces of data illustrated in the Table 2 was excluded is to improve the accuracy of the following formula (1) as a regression formula.

$$Y=153.091+0.487X1+17.714X2 \quad (1)$$

A value of Y calculated when a value of from 60° C. to 300° C. is input to X1, and a value of from 0.1 volume % to 10 volume % is input to X2 in the formula (1) is illustrated in Table 3 below.

TABLE 3

Y Calculated by Inputting Respective Values to X1 and X2 in Formula (1)

| | Oxygen Concentration X2 of Oxygen Gas in Oxidizing Step [Volume %] | | | | | |
|---|---|---|---|---|---|---|
| | 0.1 | 1 | 2 | 3 | 4 | 10 |
| Oxygen Gas Temperature X1 in Oxidizing Step [° C.] | 300 | 301 | 317 | 335 | 352 | 370 | 476 |
| | 200 | 252 | 268 | 286 | 304 | 321 | 428 |
| | 150 | 228 | 244 | 261 | 279 | 297 | 403 |
| | 100 | 203 | 219 | 237 | 255 | 273 | 379 |
| | 60 | 184 | 200 | 218 | 235 | 253 | 359 |

By collating the Table 2 and the Table 3, it is found that the temperature Y illustrated in Table 2 when the temperature X1 and the concentration X2 illustrated in the Table 2 constitute the good condition is not significantly different from the temperature Y illustrated in the Table 3 calculated using the temperature X1 and the concentration X2 of the good condition. Accordingly, the accuracy of the formula (1) as a regression formula is considered to be high.

Example 9

As illustrated in Table 4 below, an experiment was conducted similarly to the experiment of example 3 except that the process was performed up to the atmospheric exposure and the generating step was not performed.

Example 10

As illustrated in Table 4 below, an experiment was conducted similarly to the experiment of example 4 except that the process was performed up to the atmospheric exposure and the generating step was not performed.

Comparative Example 9

As illustrated in Table 4 below, an experiment was conducted similarly to the experiment of Comparative Example 2 except that the process was performed up to the atmospheric exposure and the generating step was not performed.

Comparative Example 10

As illustrated in Table 4 below, an experiment was conducted similarly to the experiment of Comparative Example 7 except that the process was performed up to the atmospheric exposure and the generating step was not performed.

[Weight Ratio Between Metallic Ni and NiO in Methanation Catalyst]

For the methanation catalyst after the atmospheric exposure in the experiments of Examples 9 and 10 and Comparative Examples 9 and 10, the weight ratio of the content of the metallic nickel to the total content of metallic nickel (metallic Ni) and nickel oxide (NiO) was obtained. Specifically, 1 g of a powder sample was extracted from the methanation catalyst after the atmospheric exposure in each example, and an X-ray diffraction (XRD) measurement was performed for the extracted powder sample, thus measuring the X-ray diffraction pattern. The XRD measurement was performed under the condition that CuKα rays were used for the powder sample under an inert atmosphere. FIG. 9 to FIG. 12 are X-ray diffraction patterns of the methanation catalyst after the atmospheric exposure in the experiments of Examples 9 and and Comparative Examples 9 and 10, respectively. As illustrated in FIG. 9 to FIG. 12, in each of Examples 9 and 10 and Comparative Examples 9 and 10, peaks of metallic nickel and nickel oxide were confirmed in the X-ray diffraction pattern of the methanation catalyst after the atmospheric exposure. Peaks of ceria were also confirmed.

Subsequently, by performing the Rietveld analysis of measurement result data of the X-ray diffraction pattern, the weight ratio [weight %] of the content of the metallic nickel and the weight ratio [weight %] of the content of the nickel oxide to the total content of metallic nickel (metallic Ni) and nickel oxide (NiO) were calculated for the methanation catalyst after the atmospheric exposure in each example. Table 4 below illustrates the result.

TABLE 4

| | | Conditions in Oxidizing Step | | | | | | | Catalyst | | |
|---|---|---|---|---|---|---|---|---|---|---|---|
| | | | | | | | Oxygen Supply Period | | | Weight Ratio Between Metallic Ni and NiO | |
| | Oxidizing Step Performed | Oxygen Gas Temperature [° C.] | Oxygen Concentration of Oxygen Gas [Volume %] | Oxygen Gas Flow Rate [L/min] | Oxygen Supply Rate [mmol-$O_2$/ sec · g-cat.] | Pressure inside Reactor [atm] | (Heat Treatment Period) [min] | Atmospheric Exposure Performed | Temperature in Atmospheric Exposure [° C.] | Metallic Ni [Weight %] | NiO [Weight %] |
| Example 9 | Yes | 100 | 1 | 10 | 0.0213 | 1 | 30 | Yes | 80 | 67 | 33 |
| Example 10 | Yes | 100 | 2 | 10 | 0.0425 | 1 | 30 | Yes | 80 | 58 | 42 |
| Comparative Example 9 | Yes | 100 | 4 | 10 | <u>0.0850</u> | 1 | 30 | Yes | 80 | 14 | 86 |
| Comparative Example 10 | <u>No</u> | — | — | — | — | — | — | Yes | 30 | 86 | 14 |

* Underlined parts indicate that values are out of ranges of conditions of the present disclosure.

By comparing the calculation result of the weight ratio illustrated in the Table 4 with the conditions of the oxidizing step enabling maintaining the catalyst performance of the methanation catalyst found from the result illustrated in the Table 4, it is considered that the weight ratios of the metallic nickel content and the weight ratios of the nickel oxide content in Examples 9 and 10 are weight ratios enabling maintaining the catalyst performance of the methanation catalyst even after the atmospheric exposure. Accordingly, from the aspect of maintaining the catalyst performance of the methanation catalyst, it is considered that the weight ratio of the metallic nickel content may be from 58 weight % to 67 weight %, and the weight ratio of the nickel oxide content may be from 42 weight % to 33 weight %.

While embodiments of the methanation catalyst processing method, the methane producing method, and the methanation catalyst of the present disclosure have been described in detail, the present disclosure is not limited to the above-described embodiments, and various kinds of changes of design are allowed within a range not departing from the spirits of the present disclosure described in the claims.

All publications, patents and patent applications cited in the present description are herein incorporated by reference as they are.

DESCRIPTION OF SYMBOLS

2 Methanation catalyst
10 Reactor
10a Gas inlet
10b Gas outlet

What is claimed is:

1. A methane producing method comprising:
oxidizing nickel through a heat treatment of a methanation catalyst by supplying an oxygen gas containing oxygen and nitrogen to a reactor, the reactor housing the methanation catalyst containing the nickel as a catalyst component;
stopping the supply of the oxygen gas to the reactor, thereby ending the oxidizing and stopping the operation of the reactor; and
generating methane by supplying a raw material gas containing carbon dioxide and hydrogen to the reactor housing the methanation catalyst in which the nickel has been oxidized in the oxidizing after the stopping of the operation of the reactor,
wherein in the oxidizing, the oxygen gas is supplied to the reactor such that the oxygen is supplied to 1 g of the methanation catalyst at a supply rate in a range of from 0.0213 mmol-$O_2$/sec·g-cat. to 0.0638 mmol-$O_2$/sec·g-cat., and a time period of the heat treatment of the methanation catalyst by supplying the oxygen gas to the reactor is set to 30 minutes or more,
wherein in the oxidizing, an oxygen concentration of the oxygen gas is in a range of from 1 volume % to 3 volume %, and a temperature of the oxygen gas at a gas inlet of the reactor is in a range of from 60° C. to 150° C., and
wherein when a temperature ° C. of the oxygen gas at the gas inlet of the reactor in the oxidizing is X1, an oxygen concentration volume % of the oxygen gas in the oxidizing is X2, and a temperature ° C. of the raw material gas at the gas inlet of the reactor when a conversion rate of the carbon dioxide in the generating is 50% is Y, formulae (1) to (4) below are satisfied $$Y = 153.091 + 0.487 X1 + 17.714 X2 \qquad (1)$$

$$160 \leq Y < 250 \qquad (2)$$

$$0 < X1 \qquad (3)$$

$$0 < X2 \qquad (4).$$

* * * * *